United States Patent
Mocikat

(12) 
(10) Patent No.: US 6,673,573 B2
(45) Date of Patent: *Jan. 6, 2004

(54) EXPRESSION OF IMMUNOGLOBULIN-CYTOKINE FUSION PROTEINS IN MALIGNANT B CELLS

(75) Inventor: Ralph Mocikat, Munich (DE)

(73) Assignee: GSF-Forschungszentrum fur Umwelt und Gesundheit, Oberschleissheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/064,026

(22) Filed: Apr. 21, 1998

(65) Prior Publication Data

US 2002/0155111 A1 Oct. 24, 2002

(30) Foreign Application Priority Data

Apr. 22, 1997 (DE) .......................... 197 16 892

(51) Int. Cl.$^7$ .................. C12N 15/62; C12N 15/13; C12N 15/90; C07K 19/00; C07K 14/52
(52) U.S. Cl. .................. 435/69.7; 435/328; 435/372.2; 435/320.1; 435/462; 435/463; 435/461; 435/455; 435/456; 435/458; 536/23.4; 536/23.5; 536/24.1; 530/387.3; 530/351
(58) Field of Search .................. 435/69.7, 328, 435/372.2, 320.1, 461, 462, 463, 455, 456, 458; 530/351, 350, 387.3; 536/23.4, 23.5, 24.1

(56) References Cited

U.S. PATENT DOCUMENTS 5,202,238 A * 4/1993 Fell, Jr. et al. ............ 435/69.6

FOREIGN PATENT DOCUMENTS

| DE | 44 06 512 C1 | 2/1995 |
| DE | 195 41 450 A1 | 5/1997 |
| WO | WO 94/04670 | 3/1994 |

OTHER PUBLICATIONS

Tao et al. Idiotype/granulocyte–macrophage colony–stimulating factor fusion protein as a vaccine for B–cell lymphoma. Nature Apr. 22, 1993;362(6422):755–8.*
Mocikat et al. Unaltered immunoglobulin expression in hybridoma cells modified by targeting of the heavy chain locus an integration vector. Immunology Jan. 1995; 84(1):159–63.*
Kardinal et al. Genetic stability of gene targeted immunoglobulin loci. I. Heavy chain isotype exhange induced by a universal gene replacement vector. Immunology Nov. 1996; 89(3):309–15.*
Taylor–Papadimitriou et al. Fusion potential for vaccines. Nature Mar./Apr. 22, 1993;362(6422):695.*
Stevenson et al. A genetic approach to idiotypic vaccination for B cell lymphoma. Annals of the New York Academy of Sciences, (Nov. 27, 1995) 772 212–26.*
Kwak et al. Induction of immune responses in patients with B–cell lymphoma against the surface–immunoglobulin idiotype expressed by their tumors. N Engl J Med Oct. 22, 1992;327(17):1209–15.*
Parmiani et al. Cytokine gene transduction in the immunotherapy of cancer. Adv Pharmacol 1997;40:259–307.*
Terness et al. Idiotypic vaccine for treatment of human B–cell lymphoma. Construction of IgG variable regions from single malignant B cells. Human Immunology, (Aug.–Sep. 1997) 56 (1–2) 17–27.*
Kimball, John W. Introduction to immunology. Macmillan, New York. 1983, pp. 27–30.*
Lang et al. Replacement–like recombination induced by an integration vector with a murine homology flank at the immunoglobulin heavy–chain locus in mouse and rat hybridoma cells. Mol Gen Genet Mar. 1994;242(5):528–38.*
Dranoff et al. Vaccination with irradiated tumor cells engineered to secrete murine granulocyte–macrophage colony–stimulating factor stimulates potent, specific, and long–lasting anti–tumor immunity. Proc Natl Acad Sci U S A. Apr. 15, 1993;90(8):3539–43.*
Kardinal et al. Integration vectors for antibody chimerization by homologous recombination in hybridoma cells. Eur J Immunol Mar. 1995;25(3):792–7.*

* cited by examiner

Primary Examiner—David S. Romeo
(74) Attorney, Agent, or Firm—Townsend and Townsend and Crew LLP

(57) ABSTRACT

According to the invention, there is provided a vector for the expression of immunoglobulin-cytokine fusion proteins in malignant B cells at least containing operably linked to each other (a) a region of at least 1.5 kb which is homologous to a region of the $\mu$ intron or the $\kappa$ intron and which lacks a functional $C_\mu$ or $C_\kappa$ enhancer or contains a non-functional $C_{s2}$ or $C_\kappa$ enhancer;

(b) at least one DNA sequence encoding a domain of an immunoglobulin or a part thereof;

(c) a DNA sequence encoding a cytokine; and (d) a marker gene selectable in eukaryotic B cells and lacking a functional enhancer region wherein the expression of said marker following integration is controlled by the cellular $C_\mu$ or $C_\kappa$ enhancer.

7 Claims, 3 Drawing Sheets

Restriction Map of Vector pSP72 (Promega, Madison, U.S.A.)

EXPRESSION OF IMMUNOGLOBULIN-CYTOKINE FUSION PROTEINS IN MALIGNANT B CELLS

The present invention relates to a vector for the expression of immunoglobulin-cytskine fusion proteins in malignant B cells, a method for the expression of immunoglobulin-cytskine fusion proteins in malignant B cells, uses of said vector as well as malignant B cells containing said vector.

BACKGROUND OF THE INVENTION

The immunoglobulin idiotype expressed on B cell lymphomas is a tumor-specific antigen which however shows a low immunogenicity in the host bearing the tumor. Several approaches have been evaluated to induce an immune reaction against the idiotype. I. a., the idiotype has been coupled to GM-CSF to be used as a soluble protein for the vaccination of mice (Nature 362, 755–758, 1993). GM-CSF is able to recruit professional antigen-presenting cells and leads to an effective presentation of the idiotype and, thus, to the activation of T cells. This approach bears the disadvantage that the immunoglobulin V genes of the lymphoma have to be cloned and the fusion protein has to be produced in vitro and purified. Therefore, this would require in a clinical situation to prepare individual vaccines for each patient.

SUMMARY OF THE INVENTION

It is an object of the present invention to provide novel vectors which may be employed universally in patients without need to prepare individual vaccines.

This object has been solved according to the invention by means of a vector for the expression of immunoglobulin-cytskine fusion proteins in malignant B cells at least containing operably linked to each other (a) a region of at least 1.5 kb which is homologous to a region of the $\mu$ intron the κ intron and which optionally contains or lacks or contains a non-functional $C_\mu$ or $C_{78}$ enhancer;

(b) at least one DNA sequence encoding a domain of an immunoglobulin or a part thereof;

(c) a DNA sequence encoding a cytskine; and (d) a marker selectable in eukaryotic B cells which optionally contains an enhancer or lacks a functional enhancer region wherein following integration the expression of this marker is controlled by the cellular $C_\mu$ or $C_\kappa$ enhancer.

Preferred embodiments of the invention become obvious from the dependent claims, the following Description as well as the Example.

DESCRIPTION OF THE PREFERRED EMBODIMENTS

Figure 1:
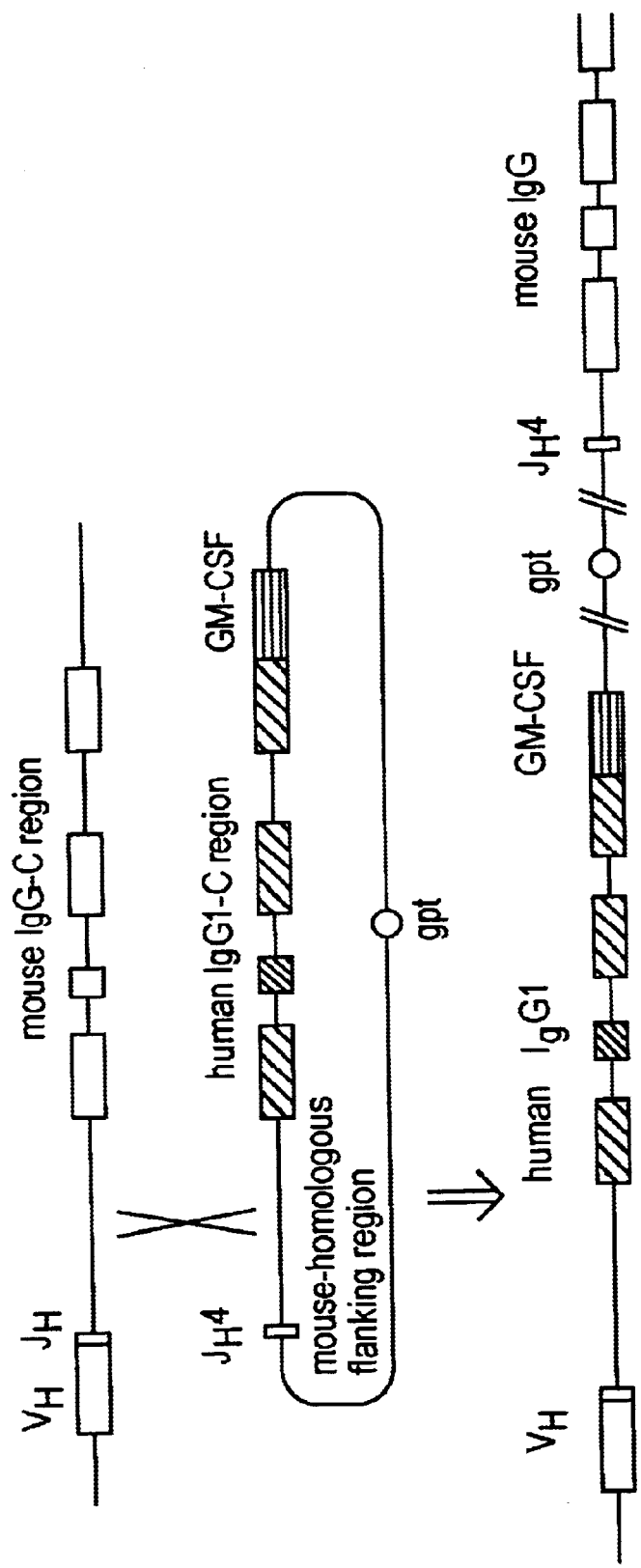
FIG. 1 is a schematic of the construct that has been integrated in a site-specific manner.

While fusion proteins obtained according to the prior art, i.e. as in the publication cited above in Nature 362, 755–758, 1993, were expressed in vitro following transfection of cell culture cells, purified, and administered in soluble form, the vectors provided according to the invention enable site-specific insertion of the cytskine gene by homologous recombination into the heavy chain locus of immunoglobulin genes without any need to isolate the V gene and to insert the gene into the vector. The vector of the invention is directly incorporated into the malignant B cell and the expression is induced in this cell, so that the genetechnological altered tumor cells may be administered directly to the patient as compared to previous approaches where it is required to administer the soluble previously purified protein. This does not only save time, effort, and costs but also leads to a significantly better tumor-protective effect.

Starting material for the construction of the vectors according to the invention were the integration vectors for the preparation of recombinant antibodies which have been described in DE 44 06 512. These vectors are useful for the highly efficient production of chimeric mouse/human antibodies. The integration vectors described in DE 44 06 512 served only for the preparation of recombinant antibodies and have therefore been expressed solely in antibody-producing hybridoma cells. The solution according to the invention to express immunoglobulins in the form of fusion proteins with cytskines by homologous recombination directly in malignant B cells and to use the malignant B cells modified in this manner for the vaccination of patients with malignant B cell tumors is not rendered obvious by DE 44 06 512.

By the present invention, a cytskine gene is introduced into the immunoglobulin heavy chain locus of malignant B cells, for example B cell lymphoma cells, via homologous recombination. For this purpose, an integration vector having the features of claim 1 has been constructed. Following site-specific integration into the heavy chain locus an immunoglobulin-cytskine fusion protein is expressed under the control of an endogenous $V_H$ promoter.

The recombination vector described may be potentially used for all lymphomas. By introduction of the cytskine gene by homologous recombination into the heavy chain locus of the malignant B cell an isolation of the idiotype may be avoided. By this, the time it takes until the start of therapy is significantly reduced. Furthermore, it is possible to use the tumor cells modified by homologous recombination after irradiation for a vaccination without having to purify the fusion protein. The following Example shows that the tumor-protective effect is much more pronounced if the vaccination is carried out using the modified cells provided according to the invention instead of the soluble protein.

Construction of the vector according to the invention is based on the integration vectors described in DE 44 06 512. For complete disclosure, this German Patent Document is incorporated herein by reference in its entirety. However, the integration vectors described in DE 44 06 512 are modified according to the invention, so that no recombinant antibodies may be expressed and recovered but that instead fusion proteins of immunoglobulin genes and cytskines which are directly expressed in malignant B cells are obtained.

The vector of the invention may have a region of at least 1.5 kb with homology to an intron region in which the Ig enhancer naturally does not occur or from which it has been deleted or in which it is inactivated; or in a further embodiment the vector according to the invention has a functional $C_\mu$ or $C_\kappa$ enhancer.

The DNA may for example comprise one or more exons as long as it encodes a functional domain of an antibody or a functional part thereof. If the functional part of the domain is a part of a V domain this must be able to bind to or to contribute to binding to the target antigen. If the functional part is a part of a C domain, this must be able to exert at least part of the effector functions.

In a preferred embodiment the region of the $\mu$ or $\kappa$ intron of at least 1.5 kb comprises the region in which the $C_\mu$ or $C_\kappa$ enhancer is localized where this region optionally contains a or lacks a functional $C_\mu$ or $C_{78}$ enhancer.

In this latter embodiment the enhancer may be either deleted or inactivated. Such an inactivation may for example be brought about by mutagenesis according to methods known from the prior art.

In the selectable marker, the enhancer has been deleted or inactivated. In another embodiment the marker lacks a natural enhancer. In a further embodiment the selectable marker contains an enhancer.

The homologous sequence contained in said vector must have a length of at least 1.5 kb to achieve a homologous recombination event at all. This DNA sequence of at least 1.5 kb may be selected from different regions of the $C_\mu$ or $C_\kappa$ intron. According to the invention, the enhancer itself may be absent from the construct or be deleted from the homologous flanking region or inactivated therein. During integration of the vector into the homologous sequence of a functionally rearranged antibody gene the expression of the recombinant gene is put under the control of an endogenous enhancer. If exons are inserted which encode the constant region these are additionally put under the control of the endogenous V promoter. Moreover, the enhancer controls the expression of the selectable marker thereby ensuring that the selection marker is only activated if it is ligated into the proximity of a strong enhancer. By the site of homology used a homologous recombination with the immunoglobulin locus is promoted whereby the selectable marker is placed under the control of the endogenous $C_{S2}$ or $C_\kappa$ enhancer.

Expression of the recombinant gene provided according to the invention coding for an immunoglobulin-cytskine fusion protein is regulated following site-specific integration 3' of the heavy chain V gene of the malignant B cell by the endogenous $V_H$ promoter.

Cloning techniques are well known to the skilled artisan from the prior art. For example, reference is made to Sambrook et al., "Molecular Cloning, A Laboratory Manual", 2nd edition 1989, Cold Spring Harbour Laboratory, Cold Spring Harbour, USA, and to Harlow and Lane, "Antibodies, A Laboratory Manual", 1988, Cold Spring Harbour Laboratory, Cold Spring Harbour, USA.

The endogenous immunoglobulin V gene segment of the immunoglobulin-producing B cells remains unchanged and is expressed after homologous recombination linked to the introduced constant gene segments as well as the cytskines. In this way, the idiotype of the B cell lymphoma is preserved, but its physical linkage to the cytskine leads to enhanced presentation by the antigen-presenting cells and thereby to an enhanced immunogenicity of the idiotype. Thus, in contrast to the vector of DE 44 06 512 the vector according to the invention does not encode a V domain or a part thereof, but instead encodes the endogenous V sequence and, thus, the idiotype of the transfected B cells is conserved.

In another preferred embodiment the vector shows a DNA sequence which encodes a constant region or a part thereof. This sequence may either encode the heavy or the light chain of an antibody. It is known to the skilled artisan that in all idiotypes several exons code for the heavy chain. If only one $C_H$ exon for the heavy chain is present in the construct this preferably is the $C_{H1}$ exon. By a construct of this type it is possible to prepare fusion proteins having an immunoglobulin portion with the functionality of Fab or F(ab)$_2$ fragments. However, the vector according to the invention preferably contains all the exons of one type of heavy chain enabling expression of a complete heavy chain. In this embodiment the elements (a), (b), (c), and (d) are arranged in this order in 5'-3' direction.

In another preferred embodiment of the integration vector according to the invention the region homologous to the $\mu$ or the $\kappa$ intron has a length of 1.9 kb or 2.0 kb.

In a further preferred embodiment the vector according to the invention contains a regulatory unit compatible to bacteria. Such a bacteria-compatible regulatory unit enables cloning and amplification of the vector in bacterial systems, for example in *E. coli*. Bacteria-compatible regulatory systems are known to the skilled artisan from the prior art; cf. Sambrook et al., as mentioned above. An example for said bacteria-compatible regulatory unit is the regulatory unit of plasmid pBR322.

In a further embodiment the immunoglobulin portion of the fusion protein is of chimeric nature. By "chimeric" there is meant an immunoglobulin which combines the V and C regions of different species. For example, a V gene from mouse may be combined with a C exon of a human isotype.

In another embodiment the DNA sequence of the feature (b) encodes a human immunoglobulin chain. This domain may be V as well as C domains or parts thereof.

In a further preferred embodiment of the vector according to the invention the DNA sequence encodes domains derived from mouse, rat, goat, horse or sheep. Preferably, all the DNA sequences for sequences encoding either the V or the C regions are derived from one of said animal species where the C regions may also be taken from different animal species.

In an advantageous embodiment of the present invention the vector bears a constant Ig region which is xenogeneic to the patient and which may be advantageous for the induction of an immune reaction.

As with the DNA sequences encoding human domains used in another embodiment of the vector of the invention, DNA sequences encoding these domains for homologous recombination may be employed together with the corresponding sequence of a different mammalian species.

In another preferred embodiment of the vector according to the invention the DNA sequence encodes all the C domains of a secretory antibody.

A further preferred embodiment of the vector according to the invention contains a DNA sequence encoding C domains of an antibody being an IgM, IgG1, IgG2a, IgG2b, IgG4, IgA, IgD, or IgE antibody. It is well known to the skilled artisan that some of these isotypes are not present in all mammalian species. For example, the human genome contains C genes encoding the IgG4 isotypes but no IgG2a or IgG2b isotypes. In contrast, the mouse genome contains C genes encoding the IgG2a and the IgG2b isotype but not the IgG4 isotype.

In a further preferred embodiment of the integration vector according to the invention the selectable marker is gpt, neo or codes for hygromycin resistance. It is known to the skilled artisan how to cultivate cells under selective conditions necessary for these markers (cf. Sambrook et al., see above). Moreover, the skilled artisan will be able to choose other selection markers which may be used in the vector according to the invention.

Transfection of immunoglobulin-producing cells is regarded as a standard procedure in modern immunology. It is well known to the skilled artisan that the transfection conditions have to be adjusted for each cell line employed. A basic course for establishing such transfection conditions is for example given in Toneguzzo et al., Mol. Cell Biol. 6 (1986), 703–706 as well as in the description for the Biorad "Genepulser". Suitable transfection conditions for mouse myeloma line NS-1 (ATCC TIB 18) are for example described in Mocikat et al., Gene 136 (1993), 349–353. Selection of stable transformants is performed by cultivation of the transformants for at least 7 days in a suitable selective medium. The selection of stable transformants is necessary to kill cells which have not incorporated the plasmid. The choice of the selective medium is of course dependent on the selection marker used. The preparation of suitable selective media is known from the prior art and may for example be found in Sambrook et al., see above.

In a preferred embodiment of the method of the invention the transfection is carried out by electroporation, calcium co-precipitation, lipofection, the DEAE dextran technique or retroviral gene transfer. All of these methods are well known from the prior art. Therefore, it is known to the skilled artisan how,to adjust the conditions for every single transfection procedure in the method according to the invention. In another preferred embodiment of the method according to the invention the selection is performed in a medium containing as the selective agent mycophenolic acid, G418 or hygromycin. As mentioned above, these selective agents are well known from the prior art. Their choice is dependent on the selection marker used while their dosage may be derived from standard text books of molecular biology; cf. Sambrook et al., see above.

In another preferred embodiment of the method according to the invention the DNA sequence encodes constant domains of the $\gamma_1$, $\gamma_{2a}$, $\gamma_{2b}$, $\gamma_3$, $\gamma_4$, $\mu$, $\alpha$, $\delta$ or $\epsilon$ isotype.

The DNA sequence according to feature (c) encodes cytskines selected from interleukins, interferons, colony-stimulating factors, lymphokines and growth factors. Examples for such DNA sequences are: IL-2, IL-4, IL-7, IL-12, IL-13, GM-CSF, or interferon $\gamma$.

The vectors of the present invention are introduced for example by the procedures characterized in more detail above into malignant B cells where they are integrated by homologous recombination and are stably expressed. By appropriate selection and identification procedures, such malignant B cells are identified which stably express the fusion protein. However, in one embodiment of the invention it is also possible to use malignant B cells containing the vector construct of the invention directly in the vaccination without previous selection of such cells which show stable expression of the fusion protein. Prior to vaccination, it is of course necessary to render the malignant B cells replication-incompetent by irradiation without affecting the expression of the fusion protein.

Thus, it is not absolutely required to perform selection of the recombinant cells prior to injection into the patient. For an anti-tumor immunization, the expression of the transformants is sufficient in which a homologous recombination event has taken place so that it is acceptable to administer a heterogenous cell population. For this reason, it is not absolutely required for the vector according to the invention to show the marker selectable in eukaryotic cells mentioned in feature (d) of claim 1. In cases, in which no selection of the recombinant cells is performed prior to injection into the patient, said marker may be omitted.

The vector provided according to the invention may also be employed in an ex vivo assay. For this purpose, cultured dendritic cells are induced to present tumor-specific peptides and optionally also to activate T cells by means of the fusion protein expressed by the recombinant tumor cells. The antigen-presenting cells or the activated T cells, respectively, would then be reintroduced into the patient.

A great advantage in the injection of such malignant B cells producing the immunoglobulin-cytskine fusion protein is that time-consuming production and purification steps for the preparation of these proteins in clinically relevant amounts become unnecessary.

The malignant B cell into which the vector according to the invention is incorporated may be for example a B cell leukemia cell, a B cell lymphoma cell, or a plasmacytoma cell.

In the following, the invention will be described referring to the Example performed using an animal model. According to continual experience, the results obtained in this manner may also be applied to humans. It should be understood that the invention is not limited to the following specific Example but may be modified in the scope of the following Claims.

EXAMPLE

Vector Construction

Figure 3:
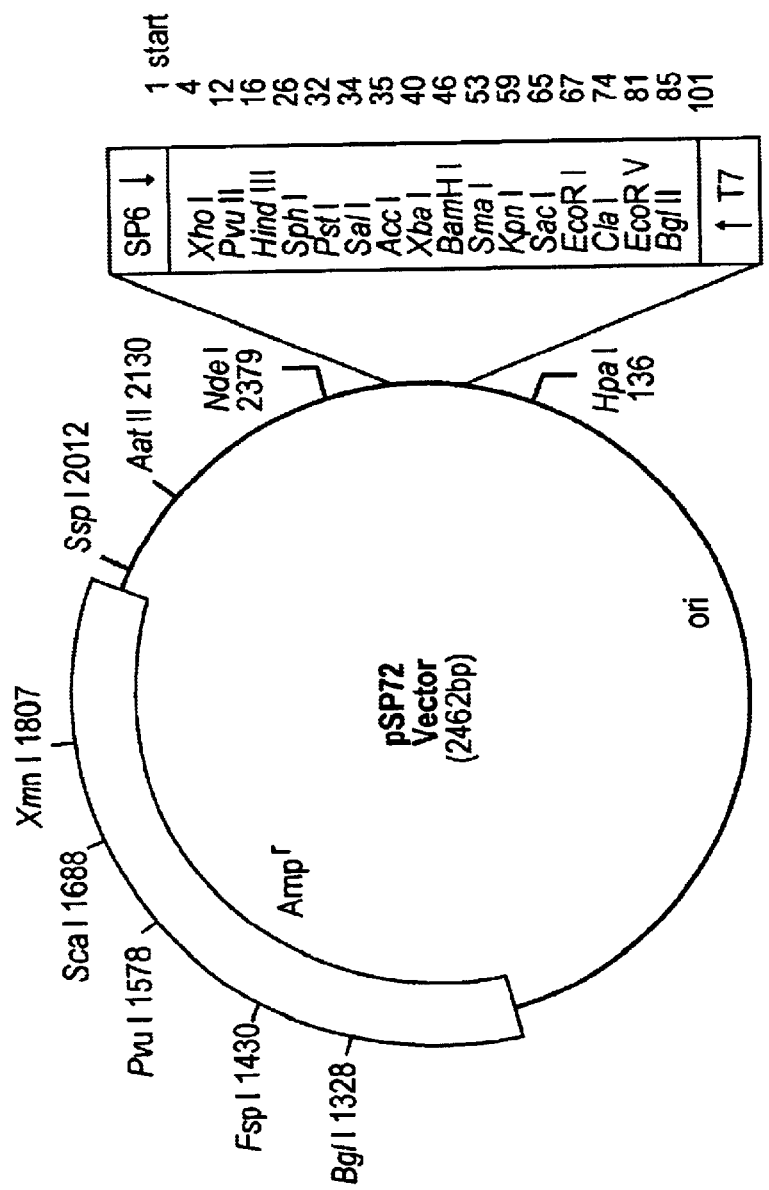
FIG. 3 is a restriction map of vector pSP72.

The murine GM-CSF gene is cloned into pSP72 (cf. FIG. 3) via PstI. The 5' portion of the gene is excised by EcoRV and XmaI and replaced by a PCR product cut by the same enzymes and lacking the 29 amino acids at the N terminus. In this manner, the construct pSP72($\Delta$EV)-GMCSF($\Delta$L) is prepared. Into vector pSVgpt-hu$\gamma$1-A5 (Kardinal et al., Eur. J. Immunol. 25, 792–797, 1995), a SalI restriction site is introduced 3' of the human IgG1-$C_H3$ exon. The GM-CSF gene is cut from pSP72($\Delta$EV)-GMCSF($\Delta$L) by SalI and ligated into the SalI site of modified pSVgpt-hu$\gamma$1-A5.

Gene Transfer

The recombination vector harbouring GM-CSF is linearized by EcoRI or BamHI and transferred into the murine B cell lymphoma cell line MPC11. Stably transfected cells are selected for the presence of the gpt gene by means of mycophenolic acid. Clones in which the construct has been integrated in site-specific manner (see FIG. 1) are identified by ELISA.

Animal Experiments

Figure 2:
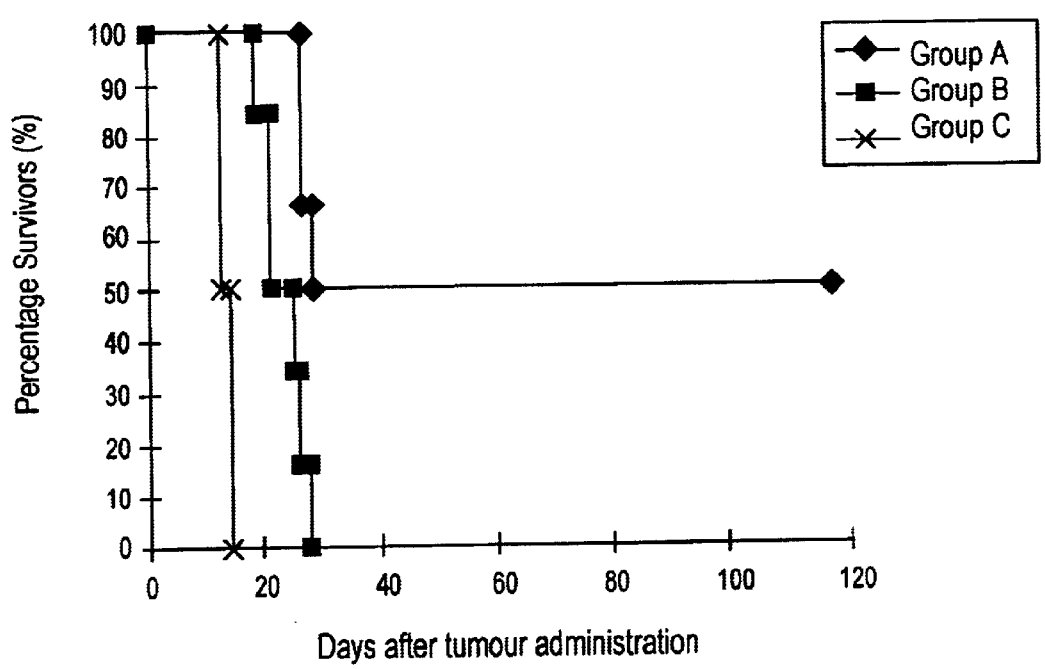
FIG. 2 is a plot showing the percent survivors vs. the number of days after tumor administration.

The benefit of the modification of a lymphoma idiotype by homologous recombination for anti-tumor immunization is demonstrated exemplarily using murine B cell lymphoma MPC11. This tumor is derived from the BALB/c mouse, it expresses IgG2b and within up to 20 days after inoculation of $10^3$ cells into syngeneic animals leads to the death of 100% of the animals. Following transfer of the vector into MPC11 and identification of homologous recombinants, these recombinants are used for immunization of BALB/c mice. For this purpose, $5\times10^6$ irradiated cells each are injected i.p. in an interval of three weeks. 7 days after the last injection a lethal inoculum of wild-type tumor cells is administered i.p. While the animals of the control group which have received only tumor cells but no pre-immunization are dying of the tumor (group C in FIG. 2), the immunized animals show a significant advantage of survival (group A). If the vaccination is performed with MPC11 cells where into the heavy chain locus only the human IgG1-C region without GM-CSF gene has been introduced by homologous recombination, i.e. which express a xenogenized heavy chain, the survival period is only marginally prolonged.

Since in the method described it is neither necessary to isolate the tumor idiotype from the lymphoma on the genetic nor on the protein level and there is no requirement for a production of individual specific vaccines but a universal vector may be employed for all lymphomas, the time until the start of therapy may be significantly reduced. Use of the irradiated tumor cells modified by homologous recombination has not only the advantage that the time-consuming and effort-consuming purification of the fusion protein may be omitted. A significant advantage is that the tumor-protective effect is much more pronounced if the immunization is carried out with cells expressing a recombinant protein as compared to administration of the purified soluble protein.

By the present recombination vector the time until the start of therapy may be considerably reduced. Furthermore, it is possible to employ the tumor cells modified by homologous recombination following irradiation for the vaccination without having to purify the fusion protein. By the Example given above, it could be demonstrated that surprisingly the tumor-protective effect is much more pronounced compared to immunization of the cells using purified soluble protein.

What is claimed is:

1. Method for the expression of an immunoglobulin-cytokine fusion protein in malignant B cells in vitro, said method comprising:
   (a) introducing into a malignant B cell a vector comprising the following components operably linked together:
      (i) a region of at least 1.5 kb which is homologous to a region of the $\mu$ intron or the $\kappa$ intron,
      (ii) at least one DNA sequence encoding a constant region of an immunoglobulin or a part of the constant region,
      (iii) a DNA sequence encoding a cytokine, and
      (iv) a marker gene which is selectable in eukaryotic B cells and contains a functional enhancer,
   whereby after homologous recombination said immunoglobulin-cytokine fusion protein is expressed, comprising the variable region of the endogenous immunoglobulin of said malignant B cell fused with said constant region of an immunoglobulin or a part of said constant region and said cytokine; and
   (b) treating the cells to render them replication-incompetent.

2. Method according to claim 1, comprising an additional step of selecting and identifying cells stably expressing the fusion protein between steps (a) and (b).

3. Method according to claim 2, wherein the selection is carried out in a medium containing mycophenolic acid, G418, or hygromycin as a selective agent.

4. Method according to claim 1, wherein step (a) is performed by means of transfection.

5. Method according to claim 4, wherein said transfection is performed by electroporation, calcium phosphate co-precipitation, lipofection, the DEAE dextran technique or by retroviral gene transfer.

6. Method according to claim 1, wherein following introduction of a vector comprising the following components operably linked together:
   (i) a region of at least 1.5 kb which is homologous to a region of the $\mu$ intron or the $\kappa$ intron,
   (ii) at least one DNA sequence encoding a constant region of an immunoglobulin or a part of the constant region,
   (iii) a DNA sequence encoding a cytokine, and
   (iv) a marker gene which is selectable in eukaryotic B cells and contains a functional enhancer,
a site-specific integration of said vector at the immunoglobulin heavy chain locus 3' of the heavy chain V gene of the malignant B cell occurs by homologous recombination.

7. Method according to claim 1, wherein the expression is controlled by the endogenous $V_H$ promoter.

* * * * *